United States Patent [19]

Noiles

[11] Patent Number: 4,865,603
[45] Date of Patent: Sep. 12, 1989

[54] METALLIC PROSTHETIC DEVICES HAVING MICRO-TEXTURED OUTER SURFACES

[75] Inventor: Douglas G. Noiles, New Canaan, Conn.

[73] Assignee: Joint Medical Products Corporation, Stamford, Conn.

[21] Appl. No.: 152,173

[22] Filed: Feb. 4, 1988

[51] Int. Cl.$^4$ .......................... A61F 2/30; B21D 31/02
[52] U.S. Cl. ....................................... 623/18; 623/16; 72/71; 72/186; 72/325
[58] Field of Search .................... 623/16–23; 72/703, 71, 186, 325; 29/DIG. 23

[56] References Cited

U.S. PATENT DOCUMENTS

| | | | |
|---|---|---|---|
| 3,605,123 | 9/1971 | Hahn . | |
| 3,781,959 | 1/1974 | O'Connor | 72/325 X |
| 3,848,273 | 11/1974 | Frey | 623/23 |
| 3,855,638 | 12/1974 | Pilliar . | |
| 3,977,026 | 8/1976 | Battault | 623/22 X |
| 4,194,384 | 3/1980 | Fujie et al. | 72/325 |
| 4,206,516 | 6/1980 | Pilliar . | |
| 4,352,212 | 10/1982 | Greene et al. . | |
| 4,411,147 | 10/1983 | Capuano | 72/469 X |
| 4,608,052 | 8/1986 | Van Kamper et al. | 623/22 |
| 4,608,053 | 8/1986 | Keller | 623/23 |
| 4,662,891 | 5/1987 | Noiles | 623/22 |
| 4,685,923 | 8/1987 | Mathys | 623/22 |

FOREIGN PATENT DOCUMENTS

WO85/03426  8/1985  PCT Int'l Appl. .

OTHER PUBLICATIONS

Cook et al., *Journal of Biomedical Materials Research*, 18, 497–512, (1984).
Yue et al., *Journal of Biomedical Materials Research*, 18, 1043–1058, (1984).

*Primary Examiner*—Alan W. Cannon
*Attorney, Agent, or Firm*—Maurice M. Klee

[57] ABSTRACT

A prosthesis for implantation in bone is provided which comprises a metal body having an outer surface at least a portion of which includes:

(a) a plurality of first recesses, each of the first recesses having a characteristic dimension of less than about 1.0 millimeter, the characteristic dimension being the minimum edge-to-edge distance across the recess at the outer surface of the prosthesis; and (b) a plurality of second recesses, each of the second recesses having a characteristic dimension less than the characteristic dimension of the first recesses.

The first recesses are created in the outer surface before the second recesses. Prior to the formation of the second recesses, the first recesses are characterized by: (1) initial areas at the outer surface; (2) initial perimeters at the outer surface; and (3) initial included angles between the outer surface and the side walls of the recess.

The second recesses are formed by depressing the outer surface of the metal body so as to deform at least some of the edges of the first recesses. The deformation produces changes in all or some of the initial areas, initial perimeters, and initial included angles. The changes give the outer surface a complex surface topography suitable for strong bonding with bone.

8 Claims, 5 Drawing Sheets

METALLIC PROSTHETIC DEVICES HAVING MICRO-TEXTURED OUTER SURFACES

BACKGROUND OF THE INVENTION

1. Field of the Invention

This invention relates to surgically implanted metallic prostheses and, in particular, to prosthetic joint implants where one or more metal components are implanted in bone.

2. Description of the Prior Art

Technological advances in prosthetic devices have benefited many people whose joints have become disabled or painful as a result of degenerative diseases, injuries or other causes. The most common and helpful present day implants comprise prostheses to replace all or part of the major weight bearing joints of the body, i.e., the hip joint and the knee joint. Disabilities to these joints severely limit a patient's activities, and thus the development of replacement prostheses for these joints has received primary attention.

Hip and knee joint protheses have been in widespread use in the United States since approximately 1971. Beginning in the early 1970's and continuing thereafter, these prostheses have been implanted using polymethylmethacrylate bone cement. Initially, this approach received widespread acceptance because it almost universally resulted in immediate relief of pain from the diseased joint.

Experience over time however has revealed that a fairly large percentage of the joints implanted with bone cement fail at 5 years and even more at 10 years after implantation. Various explanations have been offered by leading orthopedic surgeons and other experts regarding the cause of these failures. Some experts believe that the failures can be attributed to the body's non-acceptance of bone cement. Others believe that bone cement is well accepted by the body, but is not a proper structural component for use as part of a joint implant because of its physical properties.

Specifically, natural bone has a modulus of elasticity of about $1-4 \times 10^6$ p.s.i. The metals used for implants generally have a modulus of elasticity on the order of $15-35 \times 10^6$ p.s.i., that is, the metal has a considerably higher stiffness than the bone. Polymethylmethacrylate cement, on the other hand, has a modulus of elasticity on the order of $0.3-0.5 \times 10^6$ p.s.i., that is, its stiffness is less than either the metal prosthesis or the surrounding bone. Furthermore, of the three materials—cement, metal, and bone—cement has the lowest mechanical strength and fatigue properties. These physical properties of bone cement in comparison to the physical properties of the natural bone and the metal prosthesis have led many experts to believe that the source of the relatively high failure rate observed for hip and knee prostheses implanted using bone cement is mechanical failure of the cement.

Before the advent of the use of bone cement, prostheses were implanted without cement. These devices sought to achieve fixation by fibrous tissue attachment or by wedging the device into bone. In some instances, the devices included surface features having dimensions on the order of a few millimeters and up so as to try to provide interstices and lattices for engagement with either fibrous tissue or bone. These devices met with varying degrees of success. Perhaps their greatest limitation was that they were not as successful in immediately relieving pain as artificial joints implanted with cement. As a result, during the 1970's, these cementless joints were not widely used.

In the late 1970's and continuing into the 1980's, as the failure rate for cemented prostheses became apparent, interest revived in cementless joints. In particular, with regard to the present invention, efforts were made to develop prosthetic devices whose outer surfaces were porous coated so as to provide an improved interface with natural bone.

As disclosed in Hahn, U.S. Pat. No. 3,605,123, one such effort involved the idea of using plasma flame spraying to coat all or part of the outside surface of a prosthesis with a thin, overlying, porous layer of metal. As described in the Hahn patent, the preferred thickness for the layer was from about 0.015 inches to about 0.030 inches, and the pore width at the interface with bone was between 30 microns and 200 microns, with 40 microns to 70 microns considered optimum. As acknowledged in the Hahn patent, overlying a porous layer on a base metal poses a problem in providing a strong bond between the base metal and the overlying porous layer while assuring the provision of an extremely thin layer.

As an alternative to the Hahn system, as disclosed in U.S. Pat. Nos. 3,855,638 and 4,206,516, Robert Pilliar proposed a system in which at least two or three layers of small metal particles were sintered to the outside surface of the prosthesis. As described in the Pilliar patents, the porous coating created by these particles was to have a porosity between about 10 and about 40 percent and an interstitial pore size of more than 50 microns and less than about 200 microns, with the preferred pore size being between about 50 and about 100 microns.

Work through the 1970's with porous coatings established that from about 100 microns to about 500 microns is the most effective range of pore sizes into which bone may grow. This work also led to a consensus among surgeons that the following three elements are needed for a successful implantation of a porous-coated prosthesis: (1) a healthy bone; (2) a precise tight fit of the prosthesis in the cavity created in the bone: and (3) minimum motion between the prosthesis and the bone for some time after implantation to allow at least some of the healing process to take place. To minimize this motion, in the first few post-operative weeks, the patient's activity is much more limited than that permitted with cemented joint implants. With regard to the third element, it was observed that if the device moved within the bone, fibrous tissue, rather than bone, developed at the interface between the prosthesis and the bone. This fibrous tissue attachment can sometimes provide adequate fixation for the prosthesis, but in general is considered less desirable than a direct bone-prosthesis attachment.

Porous coating achieved by either plasma flame spraying or the sintering of small particles raises a number of fundamental concerns regarding the product and its function, including:

(1) The sintering processes can degrade the physical properties of the metal making up the prosthesis. To fuse small particles to the surface of the prosthesis and to one another requires raising the temperature of the prosthesis and the particles to close to their melting temperature. This heat exposure can degrade the physical fatigue properties of the underlying metal. The same is true for plasma flame spraying if a subsequent heating cycle is used to improve the bond between the coating and the substrate.

The degradation in fatigue strength is particularly severe when titanium or titanium alloys are used. See Cook et al., "Fatigue Properties of Carbon- and Porous-Coated Ti-6Al-4V Alloy," *Journal of Biomedical Materials Research*, 18, 497-512, (1984): Yue et al., "The Fatigue Strength of Porous-Coated Ti-6%Al-4%V Implant Alloy," *Journal of Biomedical Materials Research*, 18, 1043-1058, (1984): and PCT Patent Publication No. WO 85/03426, published Aug. 15, 1985 and entitled "Apparatus for Affixing a Prosthesis to Bone."

Titanium-containing materials are often preferred for use in prostheses because of their high strength, high degree of biological tolerance by the body, and their greater flexibility in comparison to cobalt-chrome alloys. Specifically, titanium alloys have approximately half the stiffness of cobalt-chrome alloys. Unfortunately, to sinter small particles to titanium-containing materials involves heating the materials to temperatures above their beta transition temperature. This heating transforms the titanium away from its preferred metallurgy and also causes the growth of large grains, which further degrades the physical properties of the metal.

(2) The flame spraying and sintering processes are difficult to control. Specifically, problems arise in achieving strong bonds between the porous coating and the underlying base metal. For example, studies on sintered porous coatings have revealed that for spherical particles having diameters in the range of 100-500 microns, the fixation spots to the substrate metal may be only on the order of 20-30% of the sphere diameter.

As a result of these difficulties in achieving strong bonds, problems arise in ensuring that the adherence of the porous layer to the surface is strong enough to function satisfactorily on the prosthesis, while, at the same time, avoiding physical dimensional changes to the prosthesis as of result of having heated the prosthesis for an extended period of time at high temperatures.

(3) The use of porous surfaces results in a many-fold increase in the area of exposed metal. Although the metals used in prostheses are accepted by the body and are generally considered to be biologically inert, some migration of ions from the metal into the body does take place. Some workers in the art feel that increasing the exposed surface area may increase this migration, and for this reason, believe that porous coating may be undesirable.

(4) In addition to the foregoing, sintering small particles to produce a porous coating results in a structure having various mechanical problems which have not been fully appreciated in the past. The particles used in these processes are commonly small spheres having diameters of between approximately 100 microns and approximately 500 microns. A typical porosity after sintering is on the order of 35%, that is, approximately 35% of the space occupied by the porous coating is available for bone ingrowth. Further, if the process is altered to increase the size of the fixation bond spots, the percentage of porosity is reduced.

Bone and metal have very different strengths, i.e., tensile, compression, and fatigue strengths. Typical strength values for bone are on the order of $1-4 \times 10^3$ p.s.i.; typical strength values, in particular, fatigue strengths for the metals used in prostheses exceed $50 \times 10^3$ p.s.i. Thus there is at least a 10 to 1 strength advantage in favor of the metal. Accordingly, since the porous structure serves as a transition zone from metal to bone, it should contain more bone than metal to provide a strength match, e.g., on the order of 10, 20, or at the most 25 percent metal. Yet, with a porosity of only 35%, there is in fact less bone than metal in the existing porous coatings, i.e., just the opposite of what would be desirable from a mechanical point of view.

SUMMARY OF THE INVENTION

In view of the foregoing state of the art, it is an object of the present invention to provide improved outer surfaces for metallic prosthetic devices and, in particular, improved outer surfaces for engagement with bone. More specifically, it is an object of the invention to provide an outer surface texture into which bone may grow which has openings or voids (recesses) which have a characteristic dimension, i.e., the smallest edge-to-edge distance across the recess at the surface of the prosthesis, smaller than a millimeter and which provide a sufficient volume for bone ingrowth so that the ratio of ingrown bone to metal at the interface can be at least one to one and can be preferably greater than one to one.

A further object of the invention is to provide such an outer surface texture by means of readily controlled processes which do not involve heating the prosthesis to elevated temperatures. More particularly, it is an object of the invention to avoid the degradation to the physical properties of the metal making up the prosthesis which occurs in the existing porous coating processes and may exist in flame spraying processes as a result of heating. Additional objects of the invention include providing such an outer surface texture (1) by mechanical processes, (2) without adding material to the surface of the prosthesis, and (3) with a minimum increase in the surface area of exposed metal. A further object of the invention is to provide such an outer surface texture on prostheses made from titanium-based metals.

To achieve the foregoing and other objects, the invention provides a prosthesis for implantation in bone comprising a metal body having an outer surface at least a portion of which includes:

(a) a plurality of first recesses, each of the first recesses having a characteristic dimension of less than about 1.0 millimeter, the characteristic dimension being the minimum edge-to-edge distance across the recess at the outer surface of the prosthesis; and (b) a plurality of second recesses, each of the second recesses having a characteristic dimension less than the characteristic dimension of the first recesses, the characteristic dimension of the second recesses being also the minimum edge-to-edge distance across the recess at the outer surface of the prosthesis.

The first recesses are created in the outer surface before the second recesses. Prior to the formation of the second recesses, the first recesses are characterized by: (1) initial areas at the outer surface; (2) initial perimeters at the outer surface; and (3) initial included angles between the outer surface and the side walls of the recess.

The second recesses are formed by depressing the outer surface of the metal body so as to deform at least some of the edges of the first recesses. The deformation produces changes in all or some of the initial areas, initial perimeters, and initial included angles. The changes give the outer surface a complex surface topography suitable for strong bonding with bone.

The accompanying drawings, which are incorporated in and constitute part of the specification, illustrate the preferred embodiments of the invention, and together with the description, serve to explain the principles of the invention. Common reference characters are used in the various drawings to designate like or corresponding parts or elements. It is to be understood, of course, that both the drawings and the description are explanatory only and are not restrictive of the invention. For example, although the invention is described in terms of a direct contact between the prosthesis and bone, it can also be used with cemented prostheses to improve the bond between the cement and the prosthesis.

DESCRIPTION OF THE PREFERRED EMBODIMENTS

As discussed above, the present invention relates to providing metallic prostheses with a micro-textured outer surface suitable for engagement with bone. In the preferred embodiments of the invention, the micro-texture is created by sequentially forming two sets of recesses in the outer surface of the prosthesis, the second set deforming the contours of the first set.

Figure 1:
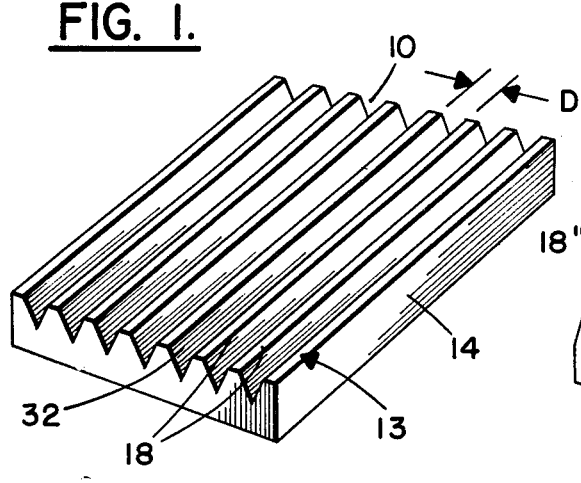
FIG. 1 is a perspective view schematically illustrating a prosthesis having first recesses formed in its outer surface.
Figure 6:
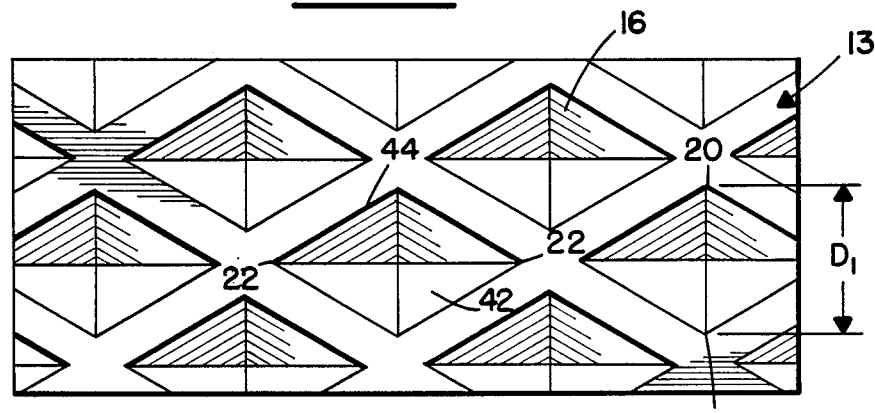
FIGS. 6 and 7 are plan views schematically illustrating the formation of coarse (FIG. 6) and fine (FIG. 7) diamond-shaped recesses in the outer surface of a prosthesis.

FIGS. 1 and 6 illustrate representative sets (pluralities) of first recesses. In FIG. 1, the recesses comprise V-shaped troughs 10 formed in outer surface 13 of body 14 of the prosthesis; in FIG. 6, the recesses comprise diamond-shaped concavities 16 formed in the outer surface. Other recess shapes, e.g., circular, elliptical, square, etc., can be used for the set of first recesses. Also, the set of first recesses need not form a uniform repeating pattern as shown in FIGS. 1 and 6, although in general, such a regular pattern is preferred.

The set of first recesses can be produced in various ways. For example, for prostheses prepared by casting, the mold used to form the prosthesis can be configured to produce the desired set of first recesses as part of the casting process. Alternatively, the set of first recesses can be produced after the body of the prosthesis has been formed. For example, the set of first recesses can be machined into the outer surface using conventional machine tools. Alternatively, a knurling tool applied to the surface of the prosthesis can be conveniently used to form the recesses. Other techniques which can be used to create the recesses include coining, electrical discharge machining, electro-chemical milling, laser metal removal techniques, and the like.

To provide a finished texture suitable for bone ingrowth, the first recesses should have a characteristic dimension, e.g., a width, at outer surface 13 of less than about 1.0 millimeter. For example, in FIG. 1, the spacing $D_1$ between edges 18 should be less than about 1.0 millimeter. Similarly, in FIG. 6, the spacing $D_1$ between corners 20 of diamond-shaped recesses 16 should be less than about 1.0 millimeter. In general, the characteristic dimension of the first recesses should be greater than about 200 microns, the preferred range for the characteristic dimension being between about 300 microns and about 700 microns.

The depths of the first recesses are generally in the same range as the characteristic dimensions. That is, the depths of the recesses are generally in the range of from about 200 microns to about 1.0 millimeter. In most cases, all of the first recesses will have approximately the same depth, although combinations of first recesses having different depths can be used if desired.

As illustrated by FIGS. 1 and 6, the length of the first set of recesses can vary widely. For example, in FIG. 1, troughs 10 have lengths many times their widths, while in FIG. 6, the lengths of the diamond-shaped recesses, measured between corners 22, are approximately twice their widths. If desired, the first recesses can have equal widths and lengths, or can be characterized by a single dimension, as in the case of circular recesses.

Figure 10:
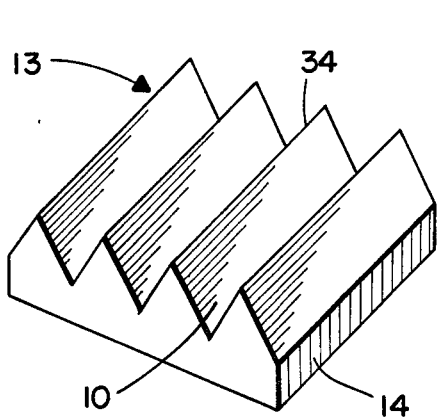
FIG. 10 is a perspective view schematically illustrating a set of first recesses similar to the first recesses of FIG. 1.

The first recesses are spaced from one another so that the recesses either share common edges, as in FIG. 10, or have spaced-apart edges, as in FIGS. 1 and 6. As discussed below in connection with FIGS. 13-15, the first recesses can also be merged with one another to form a continuous depression. Providing some surface area between the edges of the recesses is generally preferred since it aids in the formation of the second set of recesses (see below). Such surface areas should, in general, be of a smaller combined area than the combined area of the recesses, that is, most of the surface should be occupied by recesses. Put another way, the characteristic dimension of the surface areas between the recesses, e.g. the widths of those areas in FIGS. 1 and 6, should be less than the characteristic dimension of the recesses.

The set (plurality) of second recesses is formed in the outer surface of the prosthesis after the set of first recesses has been formed. Specifically, the purpose of the second recesses is to deform the first recesses so as to produce an irregular, complex surface topography having numerous voids into which bone can grow. Moreover, through the combination of the first and second recesses, open volumes are provided sufficient to produce bone to metal ratios at the bone-metal interface of 1:1 or greater.

The deformation of the first recesses is achieved by pressing the second recesses into the body of the prosthesis using a punch, knurling tool, or the like, so as to depress the surface of the metal and cause metal to flow in the regions surrounding the locations of the second recesses. The second recesses are located at or near to the edges of the first recesses so that the metal deformations produced by the formation of the second recesses will change the configurations of the first recesses.

The second recesses have a smaller characteristic dimension than the first recesses. Generally, the characteristic dimension of the second recesses is in the range of from about 25% to about 75% of the characteristic dimension of the first recesses. Similarly, the second recesses are generally shallower than the first recesses, the depth of the second recesses being between about 25% and about 75% of the depth of the first recesses. Since the second recesses are formed at locations near to the edges of the first recesses, the spacing between second recesses is a function of the spacing between first recesses. Typically, one second recess will be formed near each edge of each first recess, although more or fewer second recesses can be used as desired.

As illustrated in the figures, the second recesses can produce three types of changes to the first recesses: (1) changes in the areas of the first recesses at the outer surface; (2) changes in the perimeters of the first recesses at the outer surface; and (3) changes in the included angles between the walls of the first recesses and the outer surface. Depending on design, the second recesses can produce all three types of changes, although in some cases only one or two of the changes will be observed.

Figure 2:
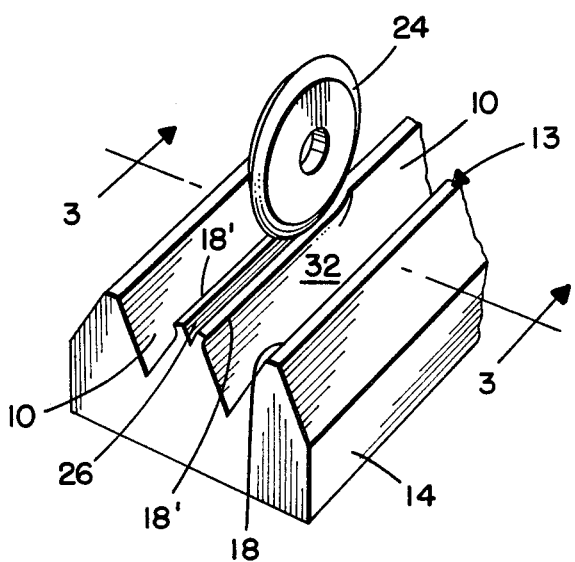

The change in the areas and perimeters of the first recesses can be seen most easily in FIG. 2. The second recesses in this case consist of shallow troughs 26 (only one shown) formed in the spaced-apart portions of surface 13 remaining after the formation of first recesses 10. The shallow troughs can be formed by, for example, pressing wheel 24 against surface 13 with sufficient force to depress the surface and cause metal to flow. The metal flow, in turn, deforms edges 18 of the first recesses to produced modified edges 18'. As shown in FIG. 2, edges 18' are closer to the center of the recesses than edges 18. Accordingly, the area of trough 10 at surface 13 has been reduced and the perimeter of that surface area has been moved inward.

Figure 4:
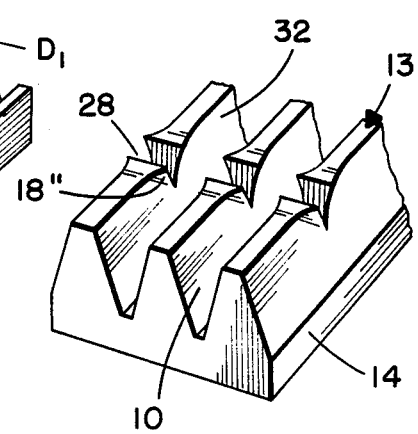
FIGS. 2, 4, and 5 are perspective views schematically illustrating various types of second recesses which can be formed in the outer surface of the prosthesis of FIG. 1.
Figure 5:
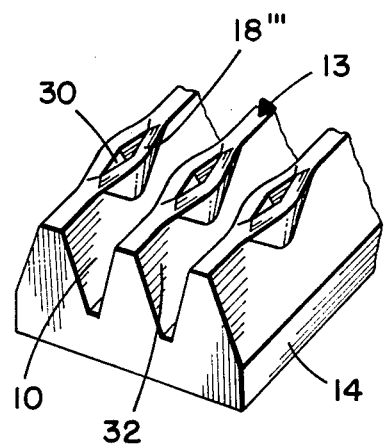

FIGS. 4 and 5 illustrate other types of second recesses which can be used to deform the first recesses of FIG. 1. In FIG. 4, the second recesses comprise V-shaped grooves 28, while in FIG. 5, they comprise diamond-shaped punctures 30. As illustrated in these figures, the second recesses deform edges 18 of first recesses 10 to produce edges 18" (FIG. 4) and edges 18''' (FIG. 5). In both cases, the deformed edges lie within the original edges and thus the formation of the second recesses reduces the areas of the first recesses at surface 13.

Figure 3:
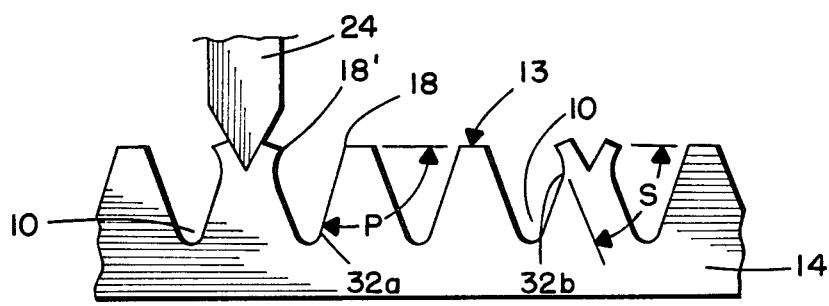
FIG. 3 is a cross-sectional view along lines 3—3 in FIG. 2.

FIG. 3 illustrates the third type of change to the first recesses which can be produced by the formation of the second recesses, namely, a change in the angle of inclination of walls 32 of the recess. As shown in this figure, prior to the formation of the second recesses, wall 32a intersects outer surface 13 at an obtuse included angle P; after the formation of the second recesses, wall 32b intersects the outer surface at an acute included angle S. Acute included angles, i.e., included angles less than 90°, will not always be produced by the formation of the second recesses. A reduction of the included angle will, however, generally be observed along the portions of walls 32 which are deformed by the second recesses. When acute included angles are created, the walls of the first recesses will become re-entrant, and thus will form an undercut-type structure which can provide a strong, interlocking bond with ingrowing bone. FIGS. 2, 4, 5, 8-9, 11-12, 14-15, and 16 further illustrate the effects of the second recesses on the inclination of the walls of the first recesses.

Figure 11:
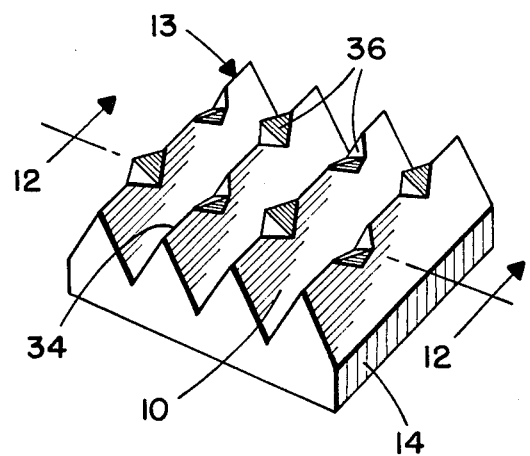
FIG. 11 is a perspective view schematically illustrating another type of second recess which can be formed in the outer surface of the prosthesis.
Figure 12:
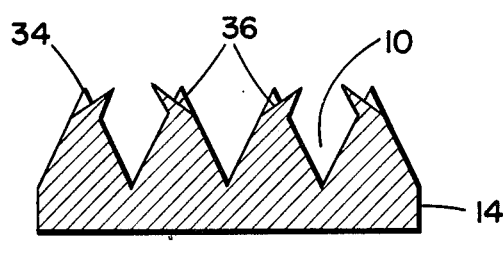
FIG. 12 is a cross-sectional view along lines 12—12 in FIG. 11.

FIGS. 10-12 illustrate an alternate embodiment wherein troughs 10 share common edges 34. The second recesses for this embodiment comprise alternating inward facing and outward facing depressions 36 of common edges 34. The depressions can conveniently be formed using a diamond-shaped punch which is first applied to even numbered troughs to produce a first row of depressions and then applied to odd numbered troughs to produce a second row of depressions, and so forth.

This embodiment illustrates one way in which the formation of the second recesses does not produce all three of the changes to the first recesses discussed above. Specifically, although the perimeters of the recesses are changed, with some portions moving inward and other portions moving outward from the initial perimeter configuration, and the wall inclinations also change, the overall surface areas of the first recesses at outer surface 13 are not changed because of the symmetrical arrangement of the second recesses.

Figure 7:
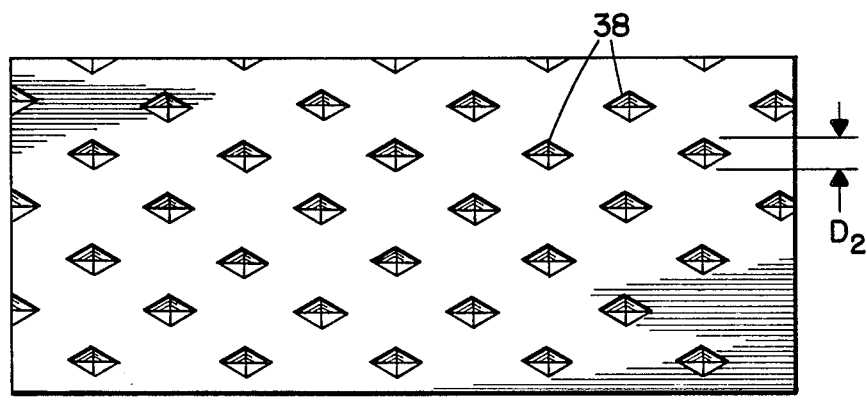
Figure 8:
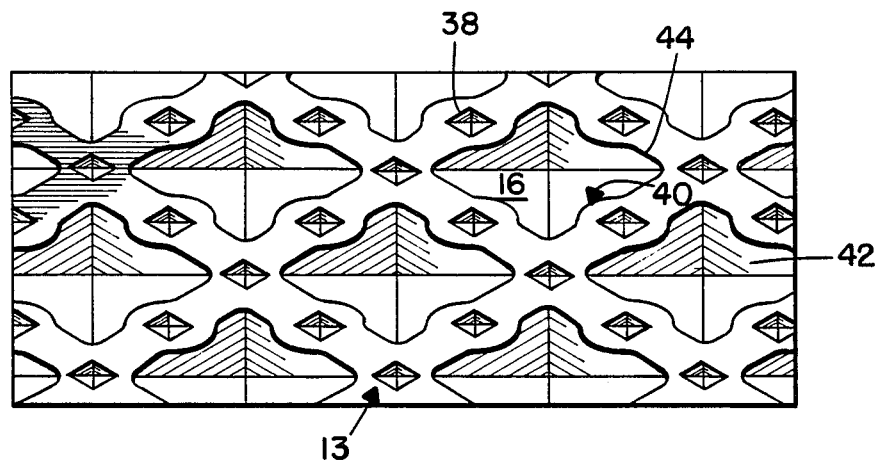
FIGS. 8 and 9 are plan and perspective views, respectively, schematically illustrating the surface topography of the outer surface of a prosthesis having both the recesses of FIG. 6 and the recesses of FIG. 7, the recesses of FIG. 7 having been created after the recesses of FIG. 6.
Figure 9:
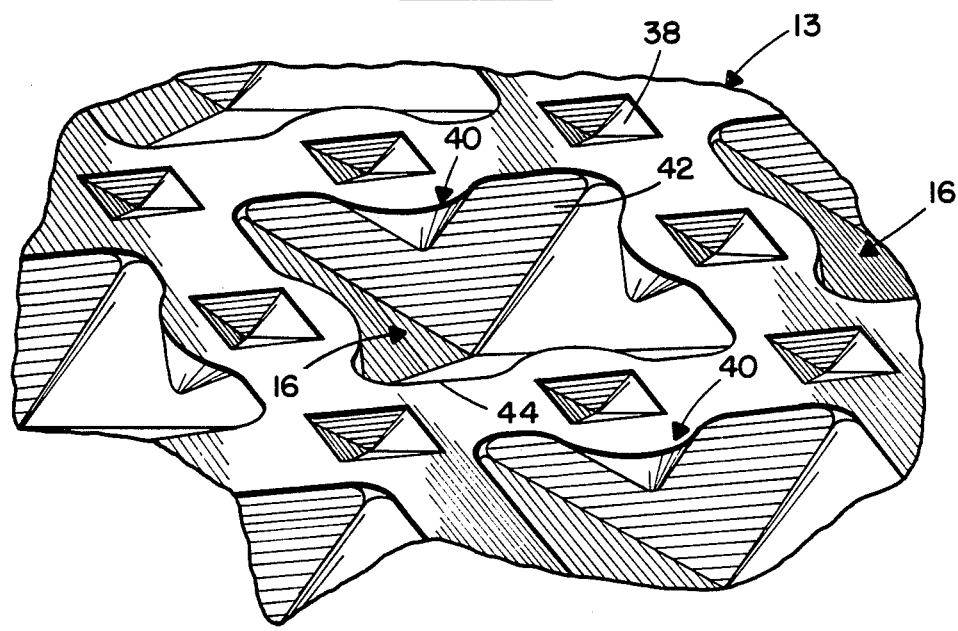

FIGS. 6-9 and 16 illustrate the use of two diamond-shaped knurling tools, having different pitches and diamond sizes, to produce first recesses 16 and second recesses 38. FIGS. 6 and 7 are schematic illustrations of the patterns produced by the first (coarse) and second (fine) knurling tools, respectively. FIGS. 8 and 9 are schematic illustrations of the combined surface produced by first applying the coarse knurling tool to the outside surface of a prosthesis and then applying the fine knurling tool to deform the recesses produced by the first knurling tool. The deformations to edges 44 and walls 42 of first recesses 16 are shown at 40 in these figures.

Figure 16:
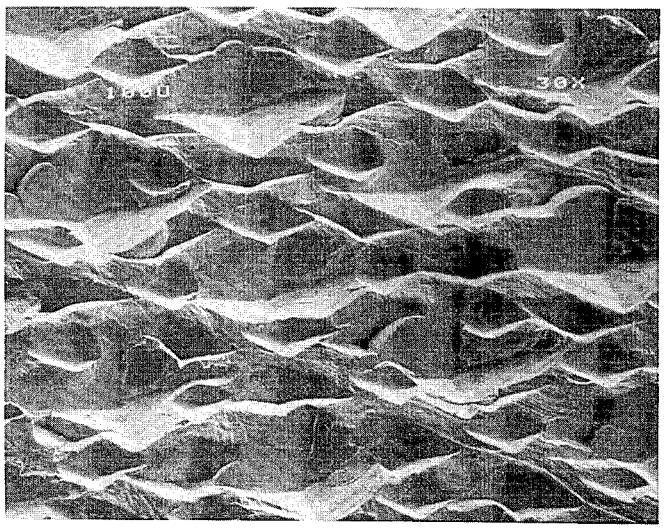
FIG. 16 is a scanning electron micrograph of the surface of a test prosthesis which has been subjected to knurling with a coarse knurling tool followed by knurling with a fine knurling tool. The surface has been magnified 30 times in this micrograph.

FIG. 16 is a scanning electron micrograph of the surface of a test prosthesis which was made from a titanium-aluminum-vanadium alloy (ASTM F136) and then surface treated in the manner illustrated in FIGS. 6-9. Specifically, the surface was first knurled with a diamond-shaped knurling tool designed to produce diamond-shaped depressions having widths of approximately 730 microns, (the characteristic dimension $D_1$ of the first recesses), lengths of approximately 1115 microns, and left/right and top/bottom spacings between the centers of the diamonds (see FIG. 6) of approximately 1735 microns and 980 microns, respectively. The first recesses were then deformed by re-knurling the surface with a diamond-shaped knurling tool designed to produce diamond-shaped depressions having widths of approximately 325 microns, (the characteristic dimension $D_2$ of the second recesses), lengths of approximately 565 microns, and left/right and top/bottom spacings between the centers of the diamonds (see FIG.

7) of approximately 1065 microns and 595 microns, respectively.

The results of this double knurling is shown in FIG. 16. As can clearly be seen in this figure, the second recesses have deformed the first recesses to produce a complex surface topography resembling ploughed ground. An examination of the first recesses shown in this figure reveals that at least to some extent, each recess has undergone all three of the area, perimeter, and wall inclination changes discussed above.

Figure 15:
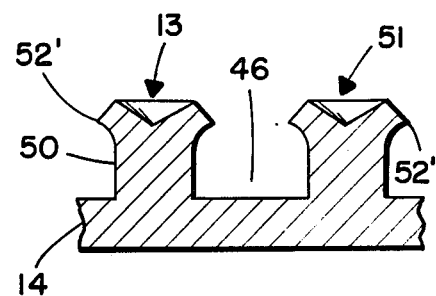
FIG. 15 is a cross-sectional view along lines 15—15 in FIG. 14.
Figure 13:
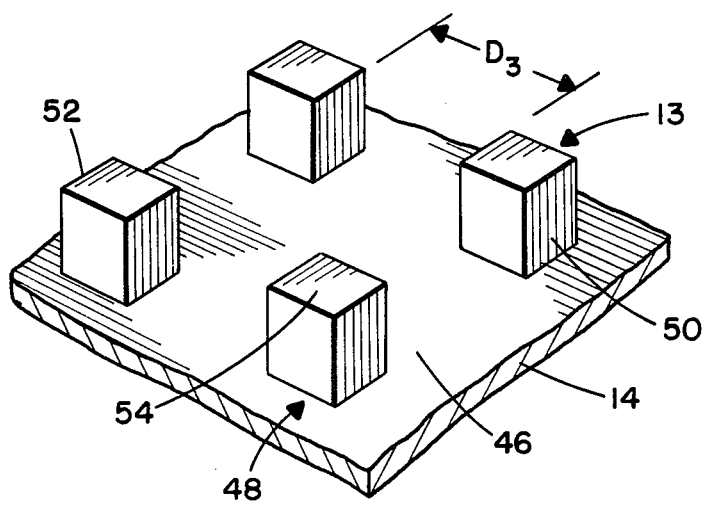
FIG. 13 is a perspective view schematically illustrating a set of continuous first recesses suitable for use with the present invention.
Figure 14:
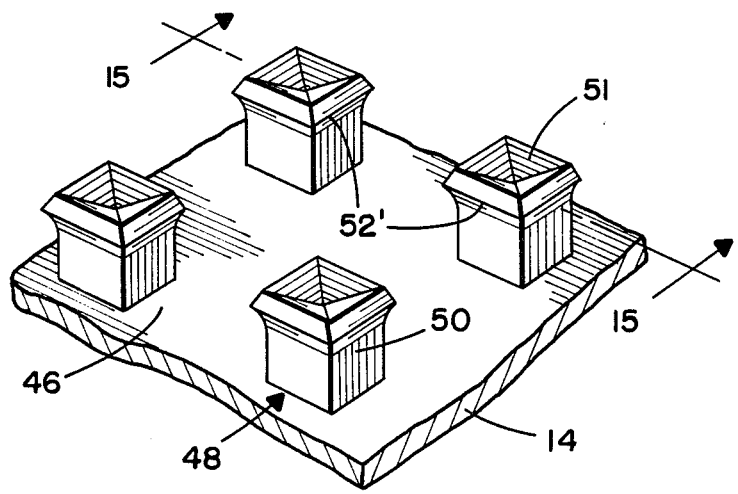
FIG. 14 is a perspective view schematically illustrating a set of second recess which can be used with the first recesses of FIG. 13.

FIGS. 13-15 show a further alternate embodiment of the present invention. In this embodiment, the first recesses have been merged with one another to form a set of continuous first recesses 46. Outer surface 13 for this embodiment comprises upper surfaces 54 of projections 48, walls 50 of the first recesses comprise the sides of the projections, top edges 52 of the walls comprise the perimeters of the first recesses, the areas between the top edges comprise the areas of the first recesses at surface 13, and the characteristic dimension of the first recesses comprises the nearest spacing between the walls, i.e., $D_3$ in FIG. 13. Second recesses 51 are formed in upper surfaces 54 of projections 48 using, for example, a contoured punch. The second recesses deform the projections resulting in changes in the inclinations and shapes of walls 50. These changes move the perimeters of the first recesses outward from the center of the projections to form perimeters 52' and thus reduce the areas of the first recesses at surface 13. Note with regard to this embodiment that projections 48 can have a variety of shapes other than that illustrated. For example, these projections can have round, elliptical, rectangular or similar cross-sections.

The micro-texture of the present invention can be used on prostheses made from various metals and metal alloys now known or subsequently developed for implant applications. The invention is of particular importance with regard to titanium-containing materials. As discussed above, because of their strength, inertness, and low stiffness, these materials are often preferred for prosthetic applications. As also discussed above, these materials are particularly susceptible to degradation by the heating steps used in, for example, the porous coating process.

With regard to degradation, titanium alloys are known to be notch sensitive and their fatigue strength is diminished by the loss of a smooth surface. Accordingly, the micro-texture of the present invention can be expected to result in some degradation in fatigue strength of titanium-containing materials. Consequently, depending on the application, it may be desirable to limit the micro-texture of the present invention to areas of prosthesis or prosthetic components which ar not subject to high cyclic stresses. See, for example, PCT Patent Publication No. WO 85/03426, referred to above.

Although specific embodiments of the invention have been described and illustrated, it is to be understood that modifications can be made without departing from the invention's spirit and scope. For example, first and second recesses having different shapes from those discussed and illustrated can be used. Similarly, the relative orientations between the various recesses can be different from the illustrative examples presented.

What is claimed is:

1. A prosthesis for implantation in bone comprising means for contributing to the support of a joint motion surface, said means being made of a biocompatible metal and having an outer surface for engagement with bone, at least a portion of said surface including:
    a plurality of first recesses, each of said first recesses having a characteristic dimension of less than about 1.0 millimeter, the characteristic dimension being the minimum edge-to-edge distance across the recess at the outer surface of the prosthesis; and
    a plurality of second recesses, each of said second recesses having a characteristic dimension which is less than the characteristic dimension of the first recesses;
    said first recesses being created in the outer surface before the second recesses, and said first recesses having initial areas at the outer surface prior to the creation of the second recesses;
    said second recesses being created by depressing the outer surface of the metal body so as to deform at least some of the edges of the first recesses; and
    said deformation reducing the areas at the outer surface of at least some of the first recesses below their initial values.

2. The prosthesis of claim 1 wherein the metal body is composed of a titanium-containing material.

3. A prosthesis for implantation in bone comprising means for contributing to the support of a joint motion surface, said means being made of a biocompatible metal and having an outer surface for engagement with bone, at least a portion of said surface including:
    a plurality of first recesses, each of said first recesses having a characteristic dimension of less than about 1.0 millimeter, the characteristic dimension being the minimum edge-to-edge distance across the recess at the outer surface of the prosthesis; and
    a plurality of second recesses, each of said second recesses having a characteristic dimension which is less than the characteristic dimension of the first recesses;
    said first recesses being created in the outer surface before the second recesses, and said first recesses having initial areas at the outer surface prior to the creation of the second recesses, said initial areas having initial perimeter configurations;
    said second recesses being created by depressing the outer surface of the metal body so as to deform at least some of the edges of the first recesses; and
    said deformation changing the perimeters of at least some of the first recesses from their initial configurations.

4. The prosthesis of claim 3 wherein for at least some of the changed perimeters, at least a portion of the changed perimeter lies with the initial perimeter.

5. The prosthesis of claim 3 wherein the metal body is composed of a titanium-containing material.

6. A prosthesis for implantation in bone comprising means for contributing to the support of a joint motion surface, said means being made of a biocompatible metal and having an outer surface for engagement with bone, at least a portion of said surface including:
    a plurality of first recesses, each of said first recesses having a characteristic dimension of less than about 1.0 millimeter, the characteristic dimension being the minimum edge-to-edge distance across the recess at the outer surface of the prosthesis; and
    a plurality of second recesses, each of said second recesses having a characteristic dimension which is less than the characteristic dimension of the first recesses;

said first recesses being created in the outer surface before the second recesses, and the side walls of the first recesses intersecting the outer surface at initial included angles prior to the creation of the second recesses;

said second recesses being created by depressing the outer surface of the metal body so as to deform at least some of the edges of the first recesses; and said deformation reducing at least some of the included angles below their initial values.

7. The prosthesis of claim 6 wherein some of the including angles are reduced below 90°.

8. The prosthesis of claim 6 wherein the metal body is composed of a titanium-containing material.

* * * * *

UNITED STATES PATENT AND TRADEMARK OFFICE
Certificate

Patent No. 4,865,603                                                                        Patented: Sept. 12, 1989

On petition requesting issuance of a certificate for correction of inventorship pursuant to 35 U.S.C. 116, it has been found that the above-identified patent, through error and without any deceptive intent, improperly sets forth the inventorship. Accordingly, it is hereby certified that the correct inventorship of this patent is:
Douglas G. Noiles and John D. Bobyn.

Signed and Sealed this Sixth Day of November 1990.

RANDALL L. GREEN

*Supervisory Primary Examiner*
                                                                       *Patent Examining Group 330*